United States Patent [19]

Davis et al.

[11] Patent Number: 5,631,248
[45] Date of Patent: May 20, 1997

[54] SUPERSATURATED TOPICAL COMPOSITIONS

[75] Inventors: Adrian F. Davis, Dorking; Jennifer J. Gordon, Godalming, both of England

[73] Assignee: SmithKline Beecham plc, England

[21] Appl. No.: 318,614

[22] PCT Filed: Apr. 2, 1993

[86] PCT No.: PCT/GB93/00692

§ 371 Date: Oct. 7, 1994

§ 102(e) Date: Oct. 7, 1994

[87] PCT Pub. No.: WO93/20799

PCT Pub. Date: Oct. 28, 1993

[30] Foreign Application Priority Data

Apr. 10, 1992 [GB] United Kingdom ............ 9207988

[51] Int. Cl.$^6$ ............................................. A61K 9/06
[52] U.S. Cl. .................... 514/179; 514/465; 514/944
[58] Field of Search ..................... 514/179, 944, 514/465

[56] References Cited

U.S. PATENT DOCUMENTS

| | | | |
|---|---|---|---|
| 4,767,751 | 8/1988 | Davis | 514/179 |
| 5,110,606 | 5/1992 | Geyer | 424/489 |

FOREIGN PATENT DOCUMENTS

| | | |
|---|---|---|
| 0151953 | 8/1985 | European Pat. Off. . |
| 6318 | 9/1968 | France . |
| 92/09266 | 6/1992 | WIPO . |

Primary Examiner—C. Warren Ivy
Assistant Examiner—Evelyn Huang
Attorney, Agent, or Firm—Nora Stein-Fernandez; William T. King; Edward T. Lentz

[57] ABSTRACT

Two-component pharmaceutical compositions for topical application to the human or animal body comprising two miscible liquid phases having different lipophilicities and a drug dissolved in at least one liquid phase, each phase comprising at least one topically acceptable non-aqueous and non-volatile solvent.

6 Claims, No Drawings

SUPERSATURATED TOPICAL COMPOSITIONS

This application is the National phase of PCT/GB93/00692, filed on Apr. 2, 1993.

The present invention relates to the topical application of active substances to the human or animal body and in particular to two-component compositions intended for mixing together either in situ on application, or immediately prior to application.

The solubility of active substances in solvent systems is important in relation to the design of topical delivery systems. It has been shown that the degree of saturation of an active substance, for example a drug, in the solvent system or vehicle is a determining factor in controlling release of the active substance.

Coldman et al.; J. Pharm. Sci., 58, 1098–1102, 1969, demonstrated that percutaneous absorption could be enhanced by over-saturating a drug solution to a supersaturated level. A supersaturated state is generated when the concentration of a solute, for example a drug, in a given solvent system exceeds the saturated solubility of the solute in that system.

Coldman prepared a solution of a drug in a mixture of a volatile and a non-volatile solvent and applied it to the surface of a sample of human skin. The volatile solvent evaporated leaving the drug in solution in the non-volatile solvent at a concentration in excess of its saturated solubility in that solvent, thereby creating a supersaturated solution in situ on the skin surface.

European Patent Publication No. 0 151 953 describes a pharmaceutical composition for generating a drug solution in a supersaturated state which is not reliant on the prior evaporation of a volatile solvent.

The composition comprises two distinct but miscible liquid phases, at least one of which contains a drug dissolved therein. The composition of the phases is such that each has a different lipophilicity (or polarity) and thus each confers a different saturated solubility on the drug. The composition of the liquid phases and the concentration of drug in one or both phases is such that on admixture of the two phases, the total drug concentration in the mixture thus formed is greater than the concentration of drug which a mixture of the same composition can accommodate as a saturated solution.

On mixing the two liquid phases, the resulting mixture is therefore supersaturated with respect to the drug.

It is an inherent property of supersaturated solutions that they will seek to adopt a more thermodynamically stable saturated state. This will generally be achieved by precipitation of solute from the supersaturated solution. The tendency for precipitation and the time scale over which it will occur will be dependent on a number of internal and external factors, including for example the degree of saturation, the nature of solute and solvents, the presence of extraneous material and the ambient temperature.

European Patent Publication No. 0 272 045 describes a pharmaceutical composition for generating a supersaturated solution wherein the tendency for drug precipitation to occur is substantially reduced by incorporation of an antinucleating agent into at least one of the liquid phases of compositions described in EP-A 0 151 953.

EP-A-0 151 953 specifically describes two-phase compositions wherein one of the liquid phases comprises water. EP-A-0 151 953 discloses the generation of supersaturated drug solutions by mixing together a lipophilic liquid phase comprising organic solvents and a polar liquid phase comprising mainly water.

It has been found that duration of the supersaturated state, generated by certain two phase compositions in accordance with EP-A 0 151 953, is limited by solvent evaporation taking place after mixing together of the two liquid phases, for example after topical administration of the resulting supersaturated drug preparation in the form of a thin film intended for long contact time usage.

Evaporation of a volatile liquid component, after mixing of the two liquid phases has been found to have, for certain compositions, the effect of increasing the saturated solubility of the drug in the resultant mixture. An increase in drug saturated solubility is reflected in a reduction of the degree of saturation of the supersaturated drug solution and a concomitant fall in the rate of percutaneous absorption.

Solvent evaporation poses a particular problem with two-phase compositions as described in EP-A 0 151 953 which are formulated with a high water content, for example hydrophilic creams and gels which are widely used in the formulation of topical preparations for delivery of topically active substances, in particular lipophilic drugs.

The problem of preferential evaporation of water from aqueous formulations, for example hydrophilic creams and gels is addressed in International Patent Publication No. WO 92/09266 (published 11 Jun. 1992), which describes a novel range of solvent systems which use coevaporation of a volatile solvent to counterbalance the effects of water loss due to evaporation.

For certain drug preparations, it is however preferable to formulate a composition intended for topical application in the absence of water. Such drug preparations are typically formulated as ointment systems or anhydrous creams. In order to enhance the percutaneous absorption of drugs from ointment-type systems, it is also desirable to formulate these systems in a form which enables the drug to be delivered to the skin surface as a supersaturated solution. Two-phase drug compositions which are able to generate a supersaturated drug solution on mixing together two non-aqueous liquid phases are provided according to the present invention.

Certain drug types are particularly suited to formulation as two-phase, non-aqueous compositions. Indeed, a non-aqueous system may be deemed necessary, for example if the drug has poor aqueous stability. Alternatively, the polarity of a drug may preclude the use of water, for example where water will be unsuitable as a carrier to promote generation of a supersaturated state. This may be especially so when low doses of drug are proposed for use.

The use of non-aqueous solvent systems does not however necessarily overcome the problem of solvent evaporation taking place after mixing together the two liquid phases. An increase in drug saturated solubility with a concomitant reduction in the degree of saturation of the supersaturated state is also observable in non-aqueous, two-phase systems comprising solvents which are volatile at ambient and particularly at body temperature and where used in thin films such that significant changes in composition may occur during use. This problem is solved according to the present invention by the use of non-volatile organic solvents in both liquid phases of a two-phase composition.

According to the present invention there is provided a two-phase composition for topical application, wherein the two phases are intended to be mixed together on or immediately prior to application, comprising:

a first liquid phase containing a drug dissolved therein and comprising a topically acceptable non-aqueous and non-volatile solubiliser; and a second liquid phase, physically and/or chemically different from the first phase but miscible therewith on admixture, optionally containing the same drug dissolved therein and comprising a topically acceptable non-aqueous and non-volatile carrier; the composition of the first and second liquid phases being such that each has a different lipophilicity and each confers a different saturated solubility on the drug; the concentration of drug in each phase in which it is present and the composition of each of the first and second liquid phases being such that, on admixture of the phases, the total drug concentration in the mixture thus formed is greater than the saturated drug concentration in the same mixture, whereby the said mixture is supersaturated with the drug.

The term drug is used herein to denote topically active substances including pharmaceutically active substances and substances conferring therapeutic and/or cosmetic benefit.

The presently claimed compositions are suitable delivery systems for a wide range of drugs for which an ointment-type or anhydrous cream topical presentation is desired. A suitable drug will be one which exhibits a variable solublity in non-aqueous solvents and solvent mixtures of differing lipophilicity. Although not a determining factor, compositions of the present invention are particularly suitable for delivery of water-sensitive drugs and drugs which are appreciably soluble in water.

The term liquid is used herein to denote materials of varying consistency ranging from non-aqueous lotions to viscous materials, in particular ointments.

It will be appreciated that compositions of the invention are not limited with respect to the physical nature of the product obtained on mixing the two liquid phases, provided that the first and second liquid phases are non-aqueous and miscible.

The second liquid phase need not contain any drug, provided that the product obtained on admixture of the two phases is supersaturated with respect to drug. Each phase may contain one or more drugs in amounts such that the resultant product mixture is supersaturated in one or more drugs.

A composition of the invention may have a first liquid phase which is saturated with drug, for example a composition of the invention may have a first liquid phase which is saturated with drug and a second liquid phase which contains no drug. The degree of saturation, and hence the rate of drug release from the resulting supersaturated drug preparation after mixing, can then be readily predicted from the saturated solubility curve for a given solubiliser/carrier system.

Due to the inefficiency of percutaneous absorption, highly supersaturated systems can be of great benefit. The rate of drug penetration in situ will depend largely on the degree of saturation, vis the ratio of supersaturated drug concentration to saturated drug concentration. A degree of saturation in excess of 1 is considered useful, and values from 2, for relatively slow penetration, to 10, for rapid penetration, are preferred. By means of the present invention very high degrees of saturation my be both obtained and moreover maintained over a substantial time period.

In a composition according to the invention, the relative proportion by weight of the first liquid phase to the second liquid phase is suitably from 1:1 to 1:12, advantageously from 1:1 to 1:10 and preferably from 1:2 to 1:8.

As used herein with respect to any composition of the invention, the term solubiliser denotes a liquid in which a drug has a higher saturated solubility than in an associated carrier.

Analogously, the term carrier denotes a liquid in which a drug has a lower saturated solubility than in an associated solubiser.

Suitably a solubiliser is a liquid in which a drug is readily soluble whilst a carrier is a liquid in which a drug has poor solubility.

Each of the first and second liquid phases may comprise more than one liquid, component.

Examples of suitable non-aqueous and non-volatile solubilisers and carriers include ethylene glycol, propylene glycol, polypropylene glycol 1,3-propylene diol, polyethylene glycol, glycerol, liquid paraffin, squalene, polydimethylsiloxane (silicone oil), lauryl alcohol, myristyl alcohol, cetyl alcohol, stearyl alcohol, oleyl alcohol, hexane-1,2,6-triol, cholesterol, lanolin, lauric acid, myristic acid, palmitic acid, stearic acid, oleic acids, vegetable oils, sorbitan esters (Spans, Arlacels), isopropyl myristate, isopropyl paimitate, tetrahydrofuryl alcohol, dimethylisosorbide, dimethylsulphoxide, benzyl alcohol, mixed triglycerides e.g. Miglyols (Tradename), modified silicones, fatty acid esters, mineral oils and other non-volatile glycerol, glycol, ether and ester solvents, for example as listed in Vaughan C. D., J. Soc. Cosmetic Chem., 36, 319–333, (1985).

Preferred solubilisers and carriers are benzyl alcohol, mixed triglycerides e.g. Miglyols and mineral oils.

It will be appreciated that a given non-aqueous solvent may be selected as a component of the solubiliser for the first liquid phase, as a component of the carrier for the second liquid phase, or alternatively as a component of both liquid phases, dependent on the lipophilicity of the drug to be incorporated in the composition relative to the lipophilicity of each liquid phase and the saturated solubility of the drug in each liquid phase.

Whilst compositions containing only non-volatile solvents avoid the potentially drying and irritant effects on the skin caused by solvent evaporation, it has been found that the texture and skin feel of ointment-type preparations generated from two-phase compositions as hereinbefore described may be enhanced by incorporation of silicone substances such as silicone oils, more particularly volatile silicone oils. The incorporation of such substances into compositions of the invention, whilst highly desirable to enhance skin feel, is however contraindicated in view of an undesirable reduction in the level of supersaturation, associated with solvent evaporation after the supersaturated drug composition has been generated by mixing, more particularly after application to the body.

This problem is overcome according to a further aspect of the present invention. It has now been found that the degree if saturation in supersaturated solutions generated from non-aqueous, two-phase pharmaceutical compositions as hereinbefore described can be sustained by using a novel range of solvent compositions which counterbalance the deleterious effects of solvent evaporation from volatile, non-aqueous materials such as volatile silicone oils.

Accordingly, in a further aspect of the present invention, there is provided a two-phase composition for topical application as hereinbefore defined, comprising non-aqueous, non-volatile solvents in each liquid phase, and further comprising a volatile solvent in each of the first and second liquid phases, whereby on admixture of the phases, the rate of loss of volatile solvent originally present in the first liquid phase is comparable to the rate of loss of volatile solvent originally present in the second liquid phase such that the ratio of the total drug concentration in the mixture to the saturated drug concentration in the same mixture remains substantially constant.

It will be appreciated that the volatile component of the topically acceptable carrier of the second liquid phase is a liquid, suitably having a lipophilicity closer to that of the non-volatile component of the carrier than that of solubilser. Similarly, the volatile component of the topically acceptable solubiliser of the first liquid phase should have a lipophilicity closer to the non-volatile component of the solubiliser than that of the carrier.

The volatile components of each liquid phase may comprise up to 20% by weight of each phase suitably from 5 to 15% by weight and preferably from 7.5 to 10% by weight.

Suitable volatile solvent components for the more lipophilic liquid phase include ethanol, isopropanol and acetone. A preferred volatile solvent component is isopropanol. A suitable, volatile solvent component for the less lipophilic liquid phase is a volatile silicone oil, for example DC 344 or DC345 (Dow Corning).

The incorporation of comparably volatile solvent components into each liquid phase further counteracts the tendency for the degree of saturation in the supersaturated preparation, generated on mixing, to decline. Co-evaporation of the volatile solvent components in each liquid phase further stabilises the lipophilicity (or polarity) of the resulting mixture and hence the drug saturated solubility.

Compositions of the invention may also contain an antinucleating agent. The antinucleating agent used in compositions according to the invention my be present in either or both of the said first and second liquid phases of the composition. Advantageously, it is present in at least the second phase and it may additionally be present in the first phase. In any event, when the two phases are mixed to provide a supersaturated solution, the antinucleating agent will, of course, be present in the resulting solution.

The antinucleating agent my be present in an amount of up to 10% by weight, suitably in an amount of up to 5.0% by weight, advantageously from 0.01 to 2.0% by weight, and preferably from 0.1 to 1.0% by weight, based on the total weight of the composition.

The antinucleating agent should be soluble or dispersible in the phase or phases in which it is present and, of course, in the resulting mixed solution.

Examples of suitable antinucleating agents are methyl cellulose, ethyl cellulose, hydroxyalkylcelluloses, such as hydroxypropylmethylcellulose and hydroxypropylcellulose, glycol esters, polyvinylpyrrolidone, polyacrylic acid, and derivatives thereof. A mixture of two or more different antinucleating agents may be used. In the event that an antinucleating agent is included in each of the first and second liquid phases of the composition, the same or different antinucleating agents may be included in each phase.

The choice of suitable antinucleating agent will depend both on the particular drug and the choice of solvent materials making up the first and second phases, but suitable anti-nucleating agents can readily be selected by simple experiment. This may be done, for example, by preparing samples of the desired final supersaturated drug solution; adding a selection of anti-nucleating agents (in say 1% by weight concentration), one to each sample; allowing the samples to stand for say 2 hours; and noting which solutions have remained clear.

Each of the first and second liquid phases may be thickened with a suitable thickening or gelling agent of either natural or synthetic origin. Examples of thickening and gelling agents are natural gums, tragacanth, carageen, pectin, agar, alginic acid, cellulose ethers and esters, xanthan gum, guar and locust bean gum, bentonite (a colloidal hydrated aiumlnium silicate), veegum (colloidal magnesium alnmluinm silicate), laponite (a synthetic hectoritc), polyvinyl alcohol, Pluronics (a Tradename), Aerosil (a Tradename colloidal silica), Carbopol (a Tradename), Plastibase (a Tradename), polyethylene, soft white paraffin, cetostearyl alcohol, cetyl and stearyl alcohol, and microcrystalline wax.

Certain thickening agents may require the addition of an adjunct which serves to activate the thickening mechanism. For example, amines are commonly used in conjunction with Carbopol suspensions.

Preservatives including anti-oxidants and UV absorbers, and other adjuvants may also be added to one or both phases.

Compositions of the invention may be prepared by processes well known in the art of pharmaceutical formulation, for example by admixture, using appropriate equipment and techniques, of the components present in each of the first and second liquid phases.

The composition of the invention may be packaged into a twin compartment pack ready for topical application by the user or patient. The user or patient would normally apply the two phases simultaneously to the treatment area and then mix the phases together in situ to create the supersaturated drug system.

The two phases may also be mixed in the pack by breaking a membrane or seal separating the first and second phases, thus creating a supersaturated solution in the pack, prior to application. Suitable packs for such purposes are commercially available.

Compositions of the invention are suitable for any medical, cosmetic or other treatment of the body surface, including the skin, scalp, nails and oral mucosa. Compositions of the invention may also be of value in delivering drugs to the systemic system by the so-called transdermal route, in which a drug is applied topically for absorption through the skin for systemic therapy.

Compositions of the invention provide a means by which many drugs which exhibit poor topical absorption, or which are required at high dosage levels, can be administered effectively in a transdermal system. Accordingly, the invention, provides a transdermal device containing a composition according to the invention.

Since a composition of the invention consists of two distinct phases, such a device will suitably comprise two compartments, for separate storage of the two phases divided by a breakable seal or membrane to allow for mixing of the two phases prior to attachment of the device to the skin surface.

In a further aspect of the invention there is provided a method for topical treatment of the human or animal body which comprises applying thereto an effective amount a pharmaceutical composition according to the invention.

Non-aqueous, two-phase compositions of the present invention as hereinbefore defined have practical utility in the field of topical drug administration, in particular where use of thin films over long contact times is necessary or advantageous and it is desirable to maintain an enhanced level of percutaneous adsorption for an extended time period. Topical administration is not limited to the skin surface but includes treatment applied to the scalp, the ocular and anogenital areas.

Suitable drugs for use in the composition and method of the invention are many and varied and include agents having the following activities:

anti-pruritics, anti-bacterials, anti-septics, anti-virals, anti-fungals, anti-psoriasis agents, anti-ache agents, anti-dandruff agents; anti-histamines, local anaesthetics, analgesics, anti-inflammatories, anti-plaque agents, beta-adrenoceptor blockers, bronchospasm relaxants, anti-angina agents, anti-travel sickness agents, decongestants, anti-tussives, anti-coagulants, head-lice treatments, anti-baldness treatments, and substances which have a beneficial effect on the skin for example in the treatment of photoageing and UV-damaged skin.

Suitable drug types include, for example, steroids, non-steroidal anti-inflammatory agents, imidazoles and retinoids, for example retinyl esters such as retinyl propionate.

The following Examples illustrate the invention. They provide two-phase formulations which on mixing the two phases generate supersaturated solutions.

In addition to the constituents described in the Examples, the first and second phases may each contain, as appropriate, adjuvants such as antinucleating agents, for example acrylates HPC, HPMC and PVP; antioxidants, for example butylated hydroxyanisole; preservatives, for example phenoxetol; gelling or thickening agents, for example Carbopol 980 with a suitable neutralising agent such as trisamino for a non-aqueous phase or sodium hydroxide for an aqueous phase; and UV absorbers, for example benzophenone-3.

|  |  | % w/w |
|---|---|---|
| Example 1 |  |  |
| First Phase: | Hydrocortisone Acetate | 0.20 |
|  | Benzyl Alcohol | 49.40 |
|  | Miglyol 810 | 49.40 |
|  | Ethyl Cellulose | 1.00 |
| Second Phase: | Mineral Oil | 100 |
| Ratio of First Phase to Second Phase = 1:9 |  |  |
| Degree of saturation on mixing = 8 |  |  |
| Example 2 |  |  |
| First Phase: | Hydrocortisone Acetate | 0.16 |
|  | Benzyl Alcohol | 30.00 |
|  | Miglyol 810 | 69.84 |
| Second Phase: | Miglyol 810 | 35.00 |
|  | Mineral Oil | 65.00 |
| Ratio of First Phase to Second Phase = 1:7 |  |  |
| Degree of saturation on mixing = 10.5 |  |  |
| Example 3 |  |  |
| First Phase: | Indomethacin | 0.40 |
|  | Benzyl Alcohol | 99.60 |
| Second Phase: | Miglyol 810 | 30.00 |
|  | Mineral Oil | 70.00 |
| Ratio of First Phase to Second Phase = 1:7 |  |  |
| Degree of saturation on mixing = 5 |  |  |
| Example 4 |  |  |
| First Phase: | Indomethacin | 0.40 |
|  | Benzyl Alcohol | 99.60 |
| Second Phase: | Miglyol 810 | 16.00 |
|  | Mineral Oil | 84.00 |
| Ratio of First Phase to Second Phase = 1:7 |  |  |
| Degree of saturation on mixing = 10 |  |  |
| Example 5 |  |  |
| First Phase: | Hydrocortisone Acetate | 0.16 |
|  | Benzyl Alcohol | 40.00 |
|  | Miglyol 810 | 59.84 |
| Second Phase: | Miglyol 810 | 35.00 |
|  | Mineral Oil | 65.00 |
| Ratio of First Phase to Second Phase = 1:7 |  |  |
| Degree of saturation on mixing = 9.5 |  |  |
| Example 6 |  |  |
| First Phase: | Indomethacin | 0.80 |
|  | Benzyl Alcohol | 99.20 |
| Second Phase: | Miglyol 810 | 43.00 |
|  | Mineral Oil | 57.00 |
| Ratio of First Phase to second Phase = 1:7 |  |  |
| Degree of saturation on mixing = 5 |  |  |

-continued

|  |  | % w/w |
|---|---|---|
| Example 7 |  |  |
| First Phase: | Indomethacin | 0.80 |
|  | Benzyl Alcohol | 99.20 |
| Second Phase: | Miglyol 810 | 30.00 |
|  | Mineral Oil | 70.00 |
| Ratio of First Phase to Second Phase = 1:7 |  |  |
| Degree of saturation on mixing = 10 |  |  |
| Example 8 |  |  |
| First Phase: | Hydrocortisone Acetate | 0.16 |
|  | Benzyl Alcohol | 44.93 |
|  | Miglyol 810 | 44.93 |
|  | Isopropyl Alcohol | 9.98 |
| Second Phase: | Mineral Oil | 90.00 |
|  | Volatile Silicone Oil (DC 344) | 10.00 |
| Ratio of First Phase to Second Phase = 1:7 |  |  |
| Degree of saturation on mixing = 6.66 |  |  |
| Degree of saturation at equilibrium = 6.72 |  |  |

EXAMPLE 9

In-vitro Release of Hydrocortisone Acetate from Saturated and Supersaturated Solutions In-vitro drug release across a thin microporous polypropylene membrane (Celgard 2500) was used as a model of drug release into the skin by percutaneous penetration. The experiment was carried out using a standard two-compartment release cell provided with a sampling port in the lower compartment through which samples of receptor phase were removed at intervals over a six hour period. The amount of drug released was assayed by HPLC.

Release of hydrocortisone acetate from a saturated (0.10% w/w) solution in propylene glycol (Sample A) was compared with release from the supersaturated solution generated by the formulation of Example 1 (Sample B).

Table 1 indicates the average total amount of drug released in two experiments, each comprising three cells for the two test solutions.

TABLE I

|  |  | Average Total Drug Released (mg) | | | |
|---|---|---|---|---|---|
| Experiment | Sample | 1 hr | 2 hr | 4 hr | 6 hr |
| 1 | A | 0.018 | — | 0.020 | 0.023 |
| 1 | B | 0.039 | 0.067 | 0.119 | 0.169 |
| 2 | A | 0.021 | 0.023 | 0.026 | 0.034 |
| 2 | B | 0.032 | 0.063 | 0.121 | 0.196 |

We claim:

1. A two-phase composition for topical application, wherein the two phases are intended to be mixed together on or immediately prior to application, comprising:
a first, non-aqueous liquid phase containing a drug dissolved therein and comprising a topically acceptable non-aqueous and non-volatile solubiliser; and a second, non-aqueous liquid phase, physically and/or chemically different from the first phase but miscible therewith on admixture, optionally containing the same drug dissolved therein and comprising a topically acceptable non-aqueous and non-volatile carrier; the composition of the first and second liquid phases being such that each has a different lipophilicity and each confers a different saturated solubility on the drug; the concentration of drug in each phase in which it is present and the composition of each of the first and second liquid phases being such that, on admixture of the phases, the total drug concentration in the mixture thus formed is greater than the saturated drug concentration in the same mixture, whereby the said mixture is supersaturated with the drug and wherein the composition further comprises a volatile solvent in each of the first and second liquid phases, whereby on admixture of the phases, the rate of loss of volatile solvent originally present in the first liquid phase is comparable to the rate of loss of volatile solvent originally present in the second liquid phase, such that the ratio of the total drug concentration in the mixture to the saturated drug concentration in the same mixture remains substantially constant.

2. A composition as claimed in claim 1 in which the volatile solvent component in each liquid phase has comparable lipophilicity to the non-volatile component in that phase.

3. A composition as claimed in claim 1 in which the volatile solvent component comprises up to 20% by weight of each of the first and second liquid phases.

4. A composition as claimed in claim 1 in which the volatile solvent component of the more lipophilic liquid phase is ethanol, isopropanol or acetone.

5. A composition as claimed in claim 1 in which the volatile solvent component of the less lipophilic liquid phase is a volatile silicone oil.

6. A composition as claimed in claim 1 in which the topically acceptable solubiliser or carrier is selected from propylene glycol, polypropylene glycol 1,3-propylene diol, polyethylene glycol, glycerol, liquid paraffin, squalene, polydimethylsiloxane (silicone oil), lauryl alcohol, myristyl alcohol, cetyl alcohol, stearyl alcohol, oleyl alcohol, hexane-1,2,6-triol, cholesterol, lanolin, lauric acid, myristic acid, palmitic acid, stearic acid, oleic acids, vegetable oils, sorbitan, isopropyl myristate, isopropyl palmitate, tetrahydrofuryl alcohol, dimethylisosorbide, dimethylsulphoxide, benzyl alcohol, mixed triglycerides, modified silicones, fatty acid esters, mineral oils and other non-volatile glycerol, glycol, ether and ester solvents.

* * * * *